United States Patent
Haddadi et al.

(10) Patent No.: US 9,223,151 B2
(45) Date of Patent: Dec. 29, 2015

(54) METHOD FOR DETERMINING READING DISTANCE

(75) Inventors: Ahmed Haddadi, Charenton-le-Pont (FR); Jean Delzers, Charenton-le-Pont (FR)

(73) Assignee: ESSILOR INTERNATIONAL (COMPAGNIE GENERALE D'OPTIQUE, Charenton-le-pont (FR)

(*) Notice: Subject to any disclaimer, the term of this patent is extended or adjusted under 35 U.S.C. 154(b) by 115 days.

(21) Appl. No.: 14/112,124

(22) PCT Filed: Mar. 8, 2012

(86) PCT No.: PCT/FR2012/050482
§ 371 (c)(1),
(2), (4) Date: Jan. 29, 2014

(87) PCT Pub. No.: WO2012/153022
PCT Pub. Date: Nov. 15, 2012

(65) Prior Publication Data
US 2014/0293219 A1    Oct. 2, 2014

(30) Foreign Application Priority Data
May 6, 2011 (FR) .................... 11 53881

(51) Int. Cl.
A61B 3/10 (2006.01)
A61B 3/14 (2006.01)
A61B 3/00 (2006.01)
G02C 13/00 (2006.01)
A61B 3/113 (2006.01)
A61B 5/103 (2006.01)

(52) U.S. Cl.
CPC ............... *G02C 13/005* (2013.01); *A61B 3/10* (2013.01); *A61B 3/113* (2013.01); *A61B 5/103* (2013.01)

(58) Field of Classification Search
USPC ................................. 351/200–246
See application file for complete search history.

(56) References Cited

U.S. PATENT DOCUMENTS

| | | | |
|---|---|---|---|
| 7,909,460 B1 * | 3/2011 | Wada | 351/204 |
| 2007/0229761 A1 | 10/2007 | Gimenez | |
| 2008/0294017 A1 | 11/2008 | Gobeyn et al. | |
| 2011/0090712 A1 | 4/2011 | Bergeron et al. | |
| 2011/0292345 A1 * | 12/2011 | Haddadi | 351/239 |

OTHER PUBLICATIONS

Search Report Dated 2011.

* cited by examiner

*Primary Examiner* — Mohammed Hasan
(74) *Attorney, Agent, or Firm* — Sofer & Haroun, LLP

(57) ABSTRACT

A method for determining reading distance for an individual made to observe a reading zone includes positioning the individual in front of an apparatus to learn their reading distance. The individual reads of a zone that is placed on a portable tablet and equipped with at least one location marker. At least one image is acquired allowing at least one facial reference point of the individual and each marker of the reading tablet. The images is processed taking into account the position of the facial reference point of the individual and the position of the at least one marker of the tablet and the indicating of the reading distance is conveyed.

8 Claims, 2 Drawing Sheets

METHOD FOR DETERMINING READING DISTANCE

RELATED APPLICATIONS

This application is a National Phase Application of PCT/FR2012/050482, tiled on Mar. 8, 2012, which in turn claims the benefit of priority from French Patent Application No. 11 53881 filed on May 6, 2011, the entirety of which are incorporated herein by reference.

BACKGROUND

1. Field of the Invention:

The invention relates to a method for determining reading distance for an individual made to read a standard text. The notion of a standard text is broad in scope because the method according to the invention must in particular be applicable to individuals who cannot read. Therefore, a standard text may include a conventional written text, or a simple graphic or a figure commonly encountered in a book or a magazine. It is important, especially for an optician, to be able to measure reading distance, in order to incorporate this parameter in production of a pair of spectacles.

For better comprehension of the description, the expressions "method for determining reading distance" and "test determining reading distance" are understood to be equivalent.

2. Description of Related Arts

Methods for determining reading distance generally rely on a summary and approximate evaluation of the latter, involving an element of guesswork and carried out without specific equipment and therefore without any particular rigor. Most of the time these methods have the unique objective of rapidly determining this distance, and do not take into account the posture adopted by the individual. However, depending on their size and body shape, each individual will be prone to incline their body and/or head to a greater or lesser degree and to adjust the orientation of the reading medium in space, in order to obtain optimal reading conditions and make themselves as comfortable as possible. In order to be rigorous, the measurement of the reading distance must incorporate all these adjustments in the position and orientation of the body and of the reading medium. The term "reading medium" is a general term and denotes any device on which a text or figures are located and may include, for example, a book or a magazine.

OBJECTS AND SUMMARY

Methods for determining reading distance according to the invention are complete and precise because, on the one hand, they take into account the posture adopted by the individual and the inclination of the reading medium, and on the other hand, they allow information relating to the reading distance to be conveyed automatically. In addition they are uses-friendly and fast, allowing the reader to adopt a comfortable reading position, without any particular constraints and without specific equipment, the reading distance being communicated to the individual immediately after the method has been implemented, just after the reading phase.

More specifically, one subject of the invention is a method for determining reading distance for an individual made to observe a reading zone, comprising the following steps:

positioning the individual in front of an apparatus designed to acquire at least one frontal image of said individual, then to process said image and lastly to convey information allowing the individual to learn their reading distance;

reading, by the individual, of said zone, which zone is placed on a portable tablet and equipped with at least one location marker, the individual adopting a natural position and adjusting the position of said tablet;

acquiring, via the apparatus, at least one image allowing at least one facial reference point of the individual and each marker of the reading tablet;

calculationally processing said at least one image, taking into account the position of the facial reference point of the individual and the position of each marker of said tablet; and conveying, via the apparatus, information indicating the reading distance.

In principle, a method according to the invention consists in capturing at least one image of the individual reading a reading zone on the tablet, then in pinpointing the position of each marker of the tablet and that of the facial reference point on said at least one image. Knowing the distance of the individual relative to the apparatus, and on the basis of angular considerations resulting from the preceding pinpointing process, it is possible to determine the reading distance with precision. It is assumed that the distance separating the facial reference point of the individual and the plane of their eyes, and the distance separating the marker and the reading zone, are known with precision in order to integrate these distances into the calculation of the reading distance. The reading tablet is a light object that can be handled with ease and on which the reading zone is located. In the case where the individual cannot read, the reading zone may take the form of a drawing or a simple figure capable advantageously of replacing a written text. Each marker of the reading tablet is placed on the front side of the latter, in order to appear in a film or on a photograph when the individual inclines said tablet in order to decipher the text and/or drawings. The apparatus may be movable or fixed in place. The reading distance may be conveyed by any possible means whether they are oral or visual, the main thing being for the information to be clear and for it to be conveyed immediately after the images have been processed, without a waiting period. The facial reference point may either be a natural reference point i.e. a part of the face that is easily pinpointabie on an image, such as the pupils of the eyes for example, or an artificial reference point located on at least one marker. As regards the reading phase in itself, no constraint is placed on the posture or position of the individual, the latter being completely free to adopt a reading posture optimized for comfort, the only limitation being that they remain facing the apparatus. In this way, the individual will find an acceptable compromise between inclination of their head and/or chest, and suitable spatial positioning of the tablet.

Preferably, the individual is wearing a pair of spectacles, and the facial reference point is marked by at least one marker securely fastened to a clip fixed to said pair of spectacles. In this way, the spectacles serve to support the markers, and the proximity of the latter to the eyes allows them to be representative of the latter in an image. The clip may bear either an individual marker positioned between the two eyes, or two markers placed in line with each eye, the number of markers not being limited. Generally, these markers are slightly offset relative to the position of the eyes, this offset being small in size and well known allowing it to be incorporated into the calculation of the reading distance.

Advantageously, the tablet is equipped with three location markers, one having a frontal position on said tablet, the two others having lateral positions. These markers allow the position of the tablet to be pinpointed in an image, in particular when said tablet is greatly inclined during the phase of reading by the individual. In other words, if the tablet were reduced to a thin part having a front side and a back side, the reading zone would be located on the backside, and the markers would be located on the front side.

Preferably, the means used to acquire the at least one image is a video camera. Specifically, a video camera is the most complete and flexible means for capturing images, allowing a continuous film to be produced and this film to be paused on specific images, allowing the best images to be selected. This type of camera also allows a number of scenes, whether zoomed in or zoomed out, to be filmed continuously one after the other.

In a first preferred embodiment of a method according to the invention, the facial reference point of the individual and each reference point of the tablet appear simultaneously in one and the same image. For this configuration it is assumed that the resolution is sufficiently high for both the facial reference point of the individual and each marker of the reading tablet to be distinguished with precision; in this case, a single frame is sufficient to determine the reading distance.

In another preferred embodiment of a method according to the invention, the video camera acquires at least two images, a first image in which at least one facial reference point of the individual appears, and a second image in which each marker of the tablet appears, the calculational processing being carried out on the basis of information gathered from said images. For this configuration it may be assumed that the resolution is not high enough from a distance, to the point that it is not possible to distinguish in one and the same snapshot the facial reference point of the individual and each marker of the tablet.

Advantageously, the video camera is moved between a first position intended for the capture of the first image and a second position intended for the capture of the second image. Specifically, it may quite simply be the case that the video camera is not able to take a sufficiently well-defined snapshot in which both the facial reference point of the individual and each marker of the reading tablet appear. Under these conditions, the video camera acquires a first shot of one of the two elements, the facial reference point or each marker of the tablet, and then is subsequently moved in order to acquire a second shot of the other element, the processing of these two images incorporating the two positions of the camera in space. Specifically, in order to be able to effectively associate the information gathered from the two snapshots, with a view to determining the reading distance, it is necessary to know the coordinates of the video camera in space at the moment these two snapshots are taken.

Advantageously, the processing of said at least one image comprises a subtraction step between a first vector connecting the facial reference point of the individual and the image acquiring camera, and a second vector connecting the reading zone on the tablet and said camera, the information being conveyed by reading it directly from a display. Said step of vector subtraction is supplemented by angular adjustments and adjustments to the vectors taking into account the various inclinations introduced during the reading phase, and offsets between the facial reference point and the plane of the eyes and between each marker of the tablet and the reading zone.

The invention also relates to a portable reading tablet for implementing a method according to the invention, said tablet comprising a face intended for reading, and at least one marker for pinpointing the spatial location of said tablet, said at least one marker being configured to allow the tablet to be located even under low-luminosity conditions. The main feature of a tablet according to the invention, is that it comprises a reading first face extended by a second face inclined at an angle of 10° to 80° relative to said first face, said second face comprising three markers, one having a frontal position, and two others having lateral positions, said three markers allowing the position of said tablet to be pinpointed in space. The reading face may either comprise a text, separate letters or numbers, or figures. Generally, this face comprises any type of characters that can be read by an individual. The marker is preferably placed on the back of this tablet relative to the reading face, in order to allow the location of said tablet to be pinpointed in a photograph, even when it is greatly inclined during reading. The geometry of the marker associated with its color must allow it to be easily and clearly pinpointed under any sort of luminosity conditions, including very low luminosity conditions.

Advantageously, the tablet comprises a reading first face extended by a second face inclined at an angle of 10° to 80° relative to said first face, said second face comprising three markers on its back, one in a frontal position, the two others having lateral positions, said three markers allowing the spatial position of said tablet to the pinpointed. The term "face" here denotes a wall. In this way, when the tablet is inclined during reading, the markers will remain clearly visible on an image or film taken from the front.

Methods for determining reading distance according to the invention have the advantage of being complete, as, in addition to providing a simple, fast and unconstraining test, they comprise an ultimate step in which the result of the test is automatically conveyed to the individual in a precise way. In addition, they have the advantage of being user-friendly, allowing the individual who is to be filmed or photographed to take center stage with spectacles equipped with a marker clip. Lastly, these methods are safe, reliable and perfectly repeatable.

BRIEF DESCRIPTION OF DRAWING

A detailed description of a preferred embodiment of a method for determining reading distance according to the invention, and of a reading tablet according to the invention, is given below with reference to FIGS. 1 to 3c.

FIG. 3b is a top view of the tablet in FIG. 3a; and

FIG. 3c is a profile view of the tablet n FIG. 3a.

DETAILED DESCRIPTION

Figure 1:
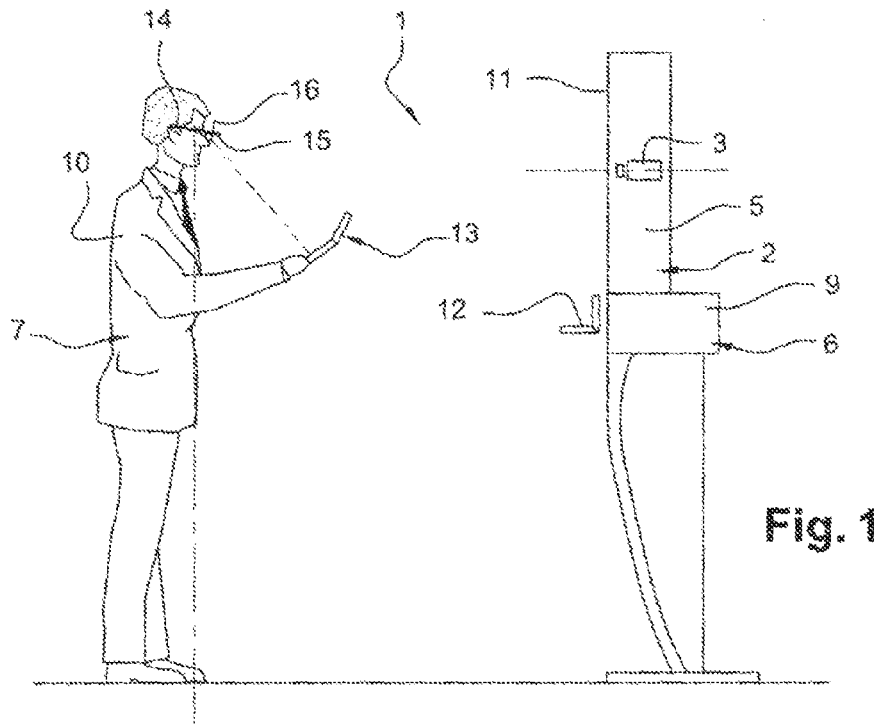
FIG. 1 is a side view of a installation provided for applying the method according to the invention, and showing an individual during a reading phase.

With reference to FIG. 1, an installation 1 intended to implement a method for determining reading distance according to the invention employs an apparatus 2 equipped with a video camera 3 allowing at least one image to be acquired, means 5 for processing said image, and means 6 for conveying said image once processed. The apparatus 2 takes the form of a fixed vertical column comprising the video camera 3, the position and height of which can be adjusted depending on the size of the individual 7 taking the test. Ideally the height of the video camera 3 is adjusted in order to be aligned horizontally with the eyes of the individual 7. The means 6 for conveying the processed image comprise a display screen 9 that may be either directly incorporated into the column 2, or connected to the latter by appropriate cables. Advantageously, the display 9 is oriented toward the individual 7, in order to allow them to see their own image directly and read, without moving, the reading distance calculated by the apparatus 2, this information appearing explicitly and instantaneously on said screen 9. The individual 7 may take the test for determining their reading distance according to the invention in a standing or sitting position, the distance separating their chest 10 from the video camera 3 being approximately 1.3 m. The column 2 comprises a flat half-silvered mirror 11 that hides the video camera 3 and allows the individual 7 to correctly position themselves in front of said column 2 with reference to their own image reflected in said mirror 11, allowing the test to be carried out under the correct conditions. In this way, the individual 7 endeavors to remain more or less in front of the column 2, and prevents themselves from deviating a significant distance therefrom. The column 2 also comprises a protruding holder 12 on which a reading tablet 13 provided for determining reading distance can be placed, this holder 12 being used between two tests. In the context of a measurement at an opticians, the individual 7 wears a frame 14 containing corrective glasses. Since the principle of the method relies at least on the acquisition of an image processed on the basis of the precise identification of the position of the plane of the eyes of the individual 7, it is therefore important to be able to rigorously pinpoint the position of a point, or zone, the location of which, relative to said plane, is known perfectly. Since it is not always possible, due to low luminosity levels, to pinpoint a natural facial reference point, the spectacles 14 are equipped with markers 15 allowing either each of the eyes 8, or a central point between said eyes 8, to be pinpointed. These markers 15 are supported by a rod 16 that can be clipped to the frame of said spectacles 14, in a substantially horizontal position, above each glass, this clip 16 possibly, for example, being analogous to that described in patent application US 2009/0262302. The apparatus may be equipped with an illuminating means allowing the ambient luminosity level to be increased and the acquisition conditions of the images to be improved. The reading phase during the method according to the invention is carried out by means of a portable reading tablet 13, this tablet being a light object of small size that the individual 7 holds in their hand and places at a certain distance from their eyes 8 in order to proceed with this phase. This tablet 13 comprises a text or drawings the size of which is analogous to the size of text or drawings that could be encountered in a book.

Figure 3A:
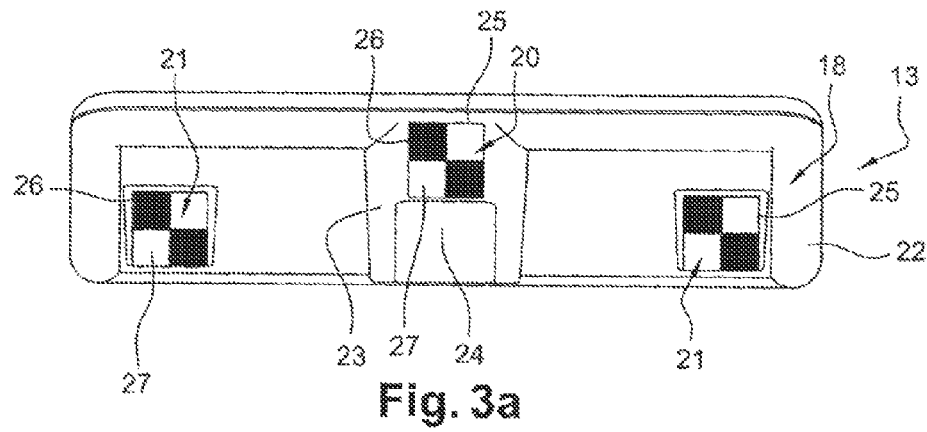
FIG. 3a is a front view of a reading tablet according to the invention.
Figure 3B:
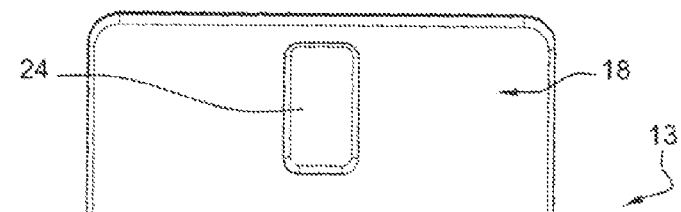
Figure 3C:
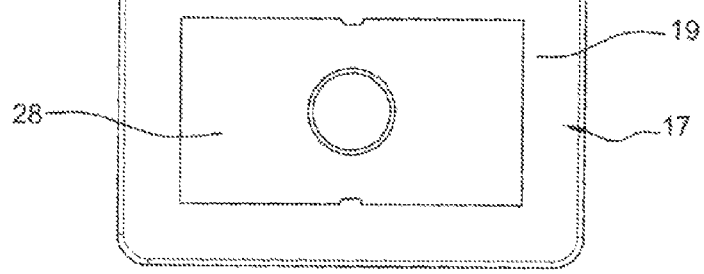

With reference to FIGS. 3a, 3b and 3c, a reading tablet 13 allowing an individual 7 to read a text during the test for determining reading distance, is an object having a small and constant thickness, and which consists of two flat and rectangular walls 17, 18 making between them an angle comprised between 10° and 80°. The first wall 17 comprises a reading face 19 on which the reading zone 28, taking the form of a text or figures; or drawings, is located. The second wall 18, which is inclined relative to the first wall 17, is equipped with three markers 20, 21, one 20 having a central and frontal position, and the two others 21 having lateral positions. More precisely, one face 22 of the second wall 18 is equipped with a central annular protuberance 23 bounding an aperture 24 that passes through said second wall 18, the marker 20 in the central position being located on said protuberance 23. If it is assumed that the second wall 18 is placed in front of the first wall 17, the central marker 20 will be located in the front-most portion of the second wall 18. The three markers 20, 21 are identical and each consist of a square 25 subdivided into four smaller squares 26, 27, two small squares 26 located on the same diagonal being darkly colored, the two others 27 located on the other diagonal being lightly colored. Advantageously, the squares 26, 27 are distinguished between by gradations of gray. Such markers 20, 21 may be easily pinpointed whatever the ambient luminosity level. These three markers 20, 21 are inclined relative to the plane of the second wall 18 and are placed on that face 22 of said second wall 18 which is opposite the face 19 of the first wall 17 comprising the reading zone 28. The inclination between the two walls 20, 21 and the positioning of the markers 20, 21 allows the position of the 20 tablet 13 to be pinpointed in a film or photograph taken by the video camera 3 during the phase of reading by the individual 7, and during which said tablet 13 runs the risk of being inclined.

Figure 2:
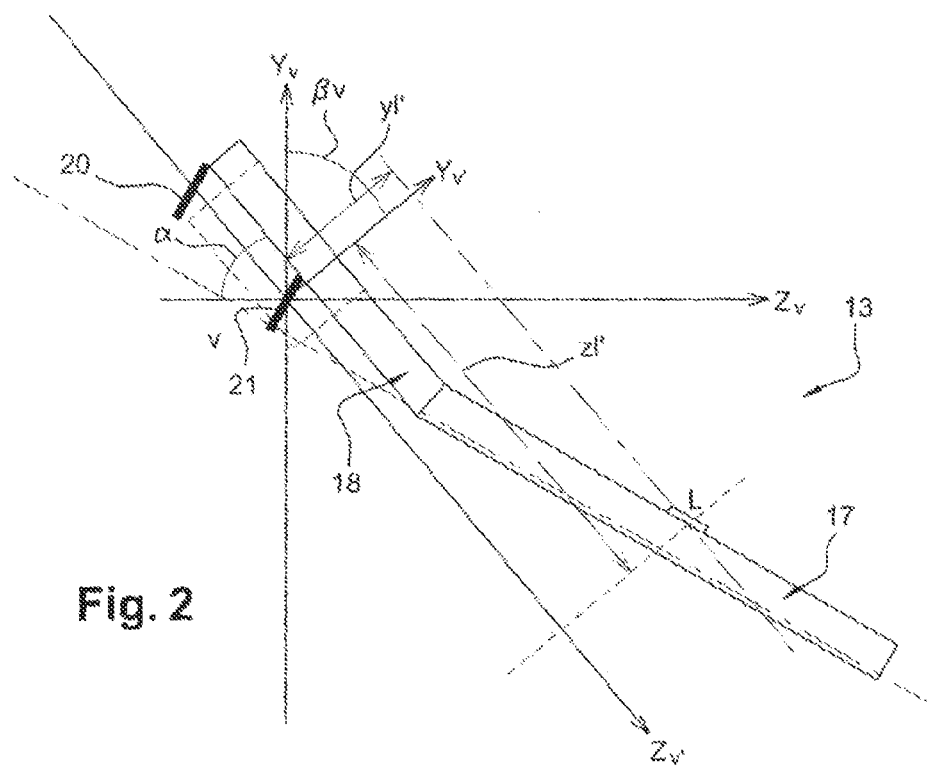
FIG. 2 is a side view of a reading tablet according to the invention, showing the various coordinates and angles linking the reading zone and the markers of the tablet.

With reference to FIG. 2, the calculational processing of the image, for determining the reading distance, first consists in determining the vector connecting the markers 15 of the clip 16 to the video camera 3, then in determining the vector connecting the markers 20, 21 of the tablet 13 to said video camera 3. These two vectors are then subtracted from each other to obtain a third vector the length of which is the distance separating the two families 15, 20, 21 of markers. Lastly, this distance is supplemented by the distances separating the markers 15 of the clip 16 from the plane of the eyes, and by the distance separating the markers 20, 21 of the tablet 13 from the reading zone 28. The distance separating the markers 15 of the clip 16 from the plane of the eyes is generally small, about a few centimeters, and may easily be measured with precision. In contrast, the vector connecting the markers 20, 21 of the tablet 13 with the reading zone 28 requires a slightly more complex calculation based on angular considerations and corrected distances, because of the inclination of said tablet 13. The principle of the method for calculating reading distance is described below:

The following prominent points are taken into consideration:

O: the optical center of the video camera 3. This is the origin of the coordinate system to which all the final measurements are transformed;

V: the geometric center of the (right and left) lateral markers 21 of the tablet 13, ($x_v$, $y_v$, $z_v$): coordinates of the point V relative to the video camera 3, i.e. relative to the point O, ($x_v'$, $y_v'$, $z_v'$): coordinate system associated with the tablet 13 and the origin of which is the point V, ($\alpha_v$, $\beta_v$, $\gamma_v$): the yaw, pitch, and roll posture of the tablet 13 relative to the video camera 3, i.e.: the respective angles of the coordinate system associated with the tablet 13 relative to the coordinate system associated with the video camera 3, allowing ($x_v$, $y_v$, $z_v$) to be aligned with ($x_v'$, $y_v'$, $z_v'$);

L: the center of the reading zone 28, ($x_l'$, $y_l'$, $z_l'$): coordinates of the point L in the coordinate system associated with the tablet 13 and the origin of which is the point V;

C: the center of the clip 16, ($x_c$, $y_c$, $z_c$): coordinates of the point C in the coordinate system associated with the video camera 3 and the origin of which is the point O, ($\alpha_c$, $\beta_c$, $\gamma_c$): angles of orientation of the clip 16 in the coordinate system associated with the video camera 3 and the origin of which is the point O; and R: center of the segment connecting the centers of rotation of the eyes, ($x_r'$, $y_r'$, $z_r'$): coordinates of the point R in the coordinate system associated with the dip 16 and the origin of which is the point C, the center of the clip 16.

The coordinate system (Xv, Yv, Zv) coincides with the coordinate system (Xv', Yv', Zv') after a rotation, the matrix of which is the product Mv=Rz (γv) Rx (βv) Ry (αv), has been applied, where:

$$R_x(\theta) = \begin{bmatrix} 1 & 0 & 0 \\ 0 & \cos\theta & -\sin\theta \\ 0 & \sin\theta & \cos\theta \end{bmatrix}$$

$$R_y(\theta) = \begin{bmatrix} \cos\theta & 0 & \sin\theta \\ 0 & 1 & 0 \\ -\sin\theta & 0 & \cos\theta \end{bmatrix}$$

$$R_z(\theta) = \begin{bmatrix} \cos\theta & -\sin\theta & 0 \\ \sin\theta & \cos\theta & 0 \\ 0 & 0 & 1 \end{bmatrix}$$

Since the coordinates of the point L are (xl', yl', zl') in the coordinate system (Xv', Yv', Zv'), the coordinates (xl, yl, zl) of the point L in the coordinate system (Xv, Yv, Zv) are calculated by applying the rotation matrix that is the inverse of Mv:

$$Mv^{-1} = Ry(-\alpha v)Rx(-\beta v)Rz(-\gamma v).$$

Decomposing the vector $\overrightarrow{OL}$ into $\overrightarrow{OV} + \overrightarrow{VL}$, the coordinates of the point L in the coordinate system of the video camera are (xv+xl, yv+yl, zv+zl), The calculation of the position of the center of the segment connecting the centers of rotation of the eyes 8 in the coordinate system of the video camera 3 follows the following steps:

Applying the method used above, the coordinate system (Xc, Yc, Zc) coincides with the coordinate system (Xc', Yc', Zc') after application of the rotation the matrix of which is the product Mc=Rz (γc) Rx (βc) Ry (αc).

Since the coordinates of the point R are (xr', yr', zr') in the coordinate system (Xc', Yc', Zc'), the coordinates (xr, yr, zr) of the point R in the coordinate system (Xc, Yc, Zc) are calculated by applying the rotation matrix that is the inverse of Mc:

$$Mc^{-1} = Ry(-\alpha c)Rx(-\beta c)Rz(-\gamma c).$$

Decomposing the vector $\overrightarrow{OR}$ into $\overrightarrow{OC} + \overrightarrow{CR}$, the coordinates of the point R in the coordinate system of the video camera are xc+xr, yc+yr, zc+zr).

The method for determining reading distance according to the invention follows the following steps:
  positioning the individual 7 in front of the column 2, with reference to their own image reflected in the mirror 11;
  reading, by the individual 7, of the reading zone 28, the individual adopting a natural and comfortable posture and adjusting the position of the tablet 13;
  acquiring, via the video camera 3, a first image in which the clip 16 equipped with its markers 15 appears, then moving said video camera 3 in order to acquire a second image in which the markers 20, 21 of the tablet 13 appear, each image being sufficiently defined for the position of the various markers 15, 20, 21 to be distinguished with precision; and
  calculational processing of the two images.
  the display 9, which is turned toward the individual, then displays the calculated reading distance, a few seconds after acquisition of the two images.

The invention is not limited to the various embodiments described above and given by way of nonlimiting examples.

The invention claimed is:

1. A portable reading tablet for implementing a method for determining reading distance, said tablet comprising;
  a face intended for reading; and
  at least one marker for pinpointing the spatial location of said tablet, said at least one marker being configured to allow the tablet to be located even under low-luminosity conditions, wherein said tablet has a reading first face extended by a second face inclined at an angle of 10° to 80° relative to said first face, and in that said second face has three markers, one having a frontal position, and two others having lateral positions, said three markers allowing the position of said tablet to be pinpointed in space.

2. A method for determining reading distance for an individual made to observe a reading zone on a tablet as claimed in claim 1, said method comprising the steps of:
  positioning the individual in front of an apparatus designed to acquire at least one frontal image of said individual, then to process said image and lastly to convey information allowing the individual to learn their reading distance;
  reading, by the individual, of said zone placed on the portable tablet, the individual adopting a natural position and adjusting the position of said tablet;
  acquiring, via the apparatus, at least one image allowing at least one facial reference point of the individual and each marker of the reading tablet;
  calculationally processing said at least one image, taking into account the position of the facial reference point of the individual and the position of said at least one marker of said tablet; and
  conveying, via the apparatus, information indicating the reading distance.

3. The method as claimed in claim 2,
  wherein the individual is wearing a pair of spectacles, and in that the facial reference point is marked by at least one marker securely fastened to a clip fixed to said pair of spectacles.

4. The method as claimed in claim 1, wherein the means used to acquire the at least one image is a video camera.

5. The method as claimed in claim 4, wherein the facial reference point of the individual and each marker of the tablet appears simultaneously in one and the same image.

6. The method as claimed in claim 4, wherein the video camera acquires at least two images, a first image in which at least one facial reference point of the individual appears, and a second image in which each marker of the tablet appears, the calculational processing being carried out on the basis of information gathered from said ages.

7. The method as claimed in claim 6, wherein the video camera is moved between a first position intended for the capture of the first image and a second position intended for the capture of the second image.

8. The method as claimed in claim 1, wherein the processing of said at least one image comprises a subtraction step between a first vector connecting the eyes of the individual with the image acquiring camera, and a second vector connecting the reading zone and said camera, and in that the information is conveyed by reading it directly from a display.

* * * * *

UNITED STATES PATENT AND TRADEMARK OFFICE
CERTIFICATE OF CORRECTION

| | | |
|---|---|---|
| PATENT NO. | : 9,223,151 B2 | Page 1 of 1 |
| APPLICATION NO. | : 14/112124 | |
| DATED | : December 29, 2015 | |
| INVENTOR(S) | : Haddadi et al. | |

It is certified that error appears in the above-identified patent and that said Letters Patent is hereby corrected as shown below:

In the Claims

Column 8, Claim 6, Line 51: The word "ages" after the word "said" should read as "images"

Signed and Sealed this
Twenty-sixth Day of April, 2016

Michelle K. Lee
*Director of the United States Patent and Trademark Office*